United States Patent
Prasad et al.

(10) Patent No.: US 9,902,963 B2
(45) Date of Patent: Feb. 27, 2018

(54) MODIFIED MICROORGANISM HAVING ENHANCED BIOMASS SYNTHESIS CAPACITY AND A METHOD THEREOF

(71) Applicant: RELIANCE INDUSTRIES LIMITED, Mumbai (IN)

(72) Inventors: Venkatesh Prasad, Mumbai (IN); Raja Kumar, Mumbai (IN); Gautam Das, Mumbai (IN); Santanu Dasgupta, Mumbai (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 15/111,554

(22) PCT Filed: Feb. 4, 2015

(86) PCT No.: PCT/IB2015/050837
§ 371 (c)(1),
(2) Date: Jul. 14, 2016

(87) PCT Pub. No.: WO2015/118457
PCT Pub. Date: Aug. 13, 2015

(65) Prior Publication Data
US 2016/0333358 A1 Nov. 17, 2016

(30) Foreign Application Priority Data
Feb. 5, 2014 (IN) .......................... 2567/MUM/2013

(51) Int. Cl.
*C12P 21/02* (2006.01)
*C12N 15/67* (2006.01)
*C07K 14/395* (2006.01)
*C12N 1/12* (2006.01)
*C12N 15/79* (2006.01)

(52) U.S. Cl.
CPC ............ *C12N 15/67* (2013.01); *C07K 14/395* (2013.01); *C12N 1/12* (2013.01); *C12N 15/79* (2013.01)

(58) Field of Classification Search
None
See application file for complete search history.

(56) References Cited

U.S. PATENT DOCUMENTS

2004/0111764 A1 6/2004 Betzner et al.

FOREIGN PATENT DOCUMENTS

WO 2003/089573 A2 10/2003

OTHER PUBLICATIONS

Tara L. Walker, et al., "Characterisation of the Dunaliella tertiolecta. RbcS genes and their promoter activity in Chlamydomonas reinhardtii.", Plant Cell Reports, (2004)1001), vol. 23, No. 10-11, p. 727-735, XP019335394 [A] 2-9, 14 Whole document DOI: http://dx.doi.org/10.1007/s00299-004-0884-x.
"Algae Expression & Engineering Products to Enhance", Your Results, (2013)114), URL:http://www.lifetechnologies.com/in/en/home/life- science /protein-biology/ rotein-expression/algal-protein-expression.html [A] 2-9, 14 Whole document.
"Chlamydomonas Protein Expression Kit", (2013)1206), URL:https://www.lifetechnologies.com/in/en-home/life-science/protein-biology/protein-expression/algal- protein-expression/chlamydomonas-protein-expression-kit.html [A] 2-9, 14 Whole document.

*Primary Examiner* — Jim Ketter
(74) *Attorney, Agent, or Firm* — Ladas & Parry LLP (57) ABSTRACT

The present disclosure provides a modified microorganism having an enhanced biomass synthesis capacity. The present disclosure also relates to a method for manufacturing a modified microorganism having an enhanced biomass synthesis capacity. The enhanced biomass synthesis capacity is due to the overexpression of the gene capable of inducing DNA repair mechanism. The gene responsible for the DNA repair is overexpressed when DNA damage is most and DNA repair mechanism is required.

14 Claims, 4 Drawing Sheets

FIGURE 1

Rad52 Sequence
ATGAATGAAATTATGGATATGGATGAGAAGAAGCCCGTTGGTAACCATTCCGAGGACATA
CAGACCAAAGACAAGAAAGGACCTGAGTATATCTCCAAGAGAGTTGGGGGAACAAGCAGG
ATTGCATACATCGAAGGTTGGAGAGTAATTAATGCTAATCAAATCGGATATAATGGCTGG
TCTACGGAGGTAAAAAGTGTAGTTATCGATGATGAGCGACAGGGAAAGAGCATAGGGTGT
ACTGCAATTGTTCGTGTTACGACTAGCGGGACTTATAGGGAAGATATTGGGTATGGTACC
GTGGAGAACGAAAGACGGAAACCTGCCGCTGAAAGGGCCAAGAAATCTGCCGTTACGGAT
GCCAAAAGATCTAGAGGGCGGTAATGCTCTAGGAAATTGTTACGATAAAGATCTGGCAAAG
ATCGATAAGGTGAAGGATCCGCCAGATGACGAAAACAATAGGCCAACGGATGAAATCAGC
GAAAGCTCAAGAACGAATACTCATGAAAATCAAGAACAACAACAATACCCGAATAAAAGA
AGGCAAACTAAAGTTACAAATACCAATCCCGACTCGACGAAGAACCTGGTGAAAATAGAA
AATACAGTAAGTCGAGGTACCCCAATGATGGCCGCACCTGCTGAGGCTAACAGTAAAAAC
AGCAGTAATAAAGATACTGATCTCAAATCTCTCGATGCTTCCAAACAGGATCAAGATGAC
CTCGATGATTCTATGAGCGATGATCAAGACGACGACATAAATATGGGCAACACAAACAGT
AATGTTACGACAGAGAAGGATCCCGTTGTAGCTAAGCAAAGCCCAACTGCTAGCTCAAAC
CCAGAGGCAGAACAAATCACCGTTACAGCTAAGGCTGCAACTTCCGTACAAAATGAACGT
TATATTGGTGAAGAGAGCATTGATCCCAAATACCAGGCACAATCCATTAGGCACACCGTT
GATCAGACTACGTCCAAGCATATTCCAGCGAGTGTGCTAAAAGACAAAACGATGACCACC
GCGAGGGATTCTGTCTATGAAAAAGCACCAAAGGGAAAACAAAGCATGAAGAACAATGAT
AAAGAACTGGGGCCTCATATGCTAGAAGGGGCTGGGAATCAAGTACCGCCTGAAACCACA
CCAATTAAAACGAACGCTACAGCTCCGCCTGCAGCTGCTCCACGGGCGCCGCCTTCTAAG
GTAGTACATCCTAATGGAAATGGTGCAGTGCCAGCCGTTCCGCAACAAAGATCGACACGA
AGAGAAGTTGGAAGACCAAAGATCAATCCCCTGCATGCACGCAAGCCTACTTGA

SEQUENCE LISTING

```
<160> NUMBER OF SEQ ID NOS: 01

<210> SEQ ID NO 1
<211> LENGTH: 1314
<212> TYPE: DNA
<213> ORGANISM: Saccharomyces_cerevisiae

<400> SEQUENCE: 1
atgaatgaaa ttatggatat ggatgagaag aagcccgttg gtaaccattc cgaggacata      60
cagaccaaag acaagaaagg acctgagtat atctccaaga gagttggggg aacaagcagg     120
attgcataca tcgaaggttg gagagtaatt aatgctaatc aaatcggata taatggctgg     180
tctacggagg taaaaagtgt agttatcgat gatgagcgac agggaaagag catagggtgt     240
actgcaattg ttcgtgttac gactagcggg acttataggg aagatattgg gtatggtacc     300
gtggagaacg aaagacggaa acctgccgct gaaagggcca agaaatctgc cgttacggat     360
gccaaaagat ctagaggggg taatgctcta ggaaattgtt acgataaaga tctggcaaag     420
```

-continued

```
atcgataagg tgaaggatcc gccagatgac gaaaacaata ggccaacgga tgaaatcagc    480
gaaagctcaa gaacgaatac tcatgaaaat caagaacaac aacaataccc gaataaaaga    540
aggcaaacta aagttacaaa taccaatccc gactcgacga agaacctggt gaaaatagaa    600
aatacagtaa gtcgaggtac cccaatgatg gccgcacctg ctgaggctaa cagtaaaaac    660
agcagtaata aagatactga tctcaaatct ctcgatgctt ccaaacagga tcaagatgac    720
ctcgatgatt ctatgagcga tgatcaagac gacgacataa atatgggcaa cacaaacagt    780
aatgttacga cagagaagga tcccgttgta gctaagcaaa gcccaactgc tagctcaaac    840
ccagaggcag aacaaatcac cgttacagct aaggctgcaa cttccgtaca aaatgaacgt    900
tatattggtg aagagagcat tgatcccaaa taccaggcac aatccattag gcacaccgtt    960
gatcagacta cgtccaagca tattccagcg agtgtgctaa aagacaaaac gatgaccacc   1020
gcgagggatt ctgtctatga aaaagcacca aagggaaaac aaagcatgaa gaacaatgat   1080
aaagaactgg ggcctcatat gctagaaggg gctgggaatc aagtaccgcg tgaaaccaca   1140
ccaattaaaa cgaacgctac agctccgcct gcagctgctc cacgggcgcc gccttctaag   1200
gtagtacatc ctaatggaaa tggtgcagtg ccagccgttc cgcaacaaag atcgacacga   1260
agagaagttg gaagaccaaa gatcaatccc ctgcatgcac gcaagcctac ttga         1314
```

MODIFIED MICROORGANISM HAVING ENHANCED BIOMASS SYNTHESIS CAPACITY AND A METHOD THEREOF

RELATED APPLICATION INFORMATION

This application is a 371 of International Application PCT/IB2015/050837, filed 4 Feb. 2015, which claims priority from India Application No.: 2567/MUM/2013 filed 5 Feb. 2014, the content of which is incorporated herein by reference.

FIELD

The present disclosure relates to a modified microorganism having enhanced biomass synthesis capacity and a method for manufacturing the modified microorganism.

BACKGROUND

Microorganisms such as algae are constantly exposed to harsh environmental conditions during their life cycle. The harsh environmental conditions include abiotic stresses such as ultraviolet radiation (UV), salinity, light, unfavorable temperature, alkalinity, nutrient limitation, oxidative stress, senescence, sulfur deficiency, carbon deficiency, nitrogen use inefficiency and the like. Biotic stresses include infection by virus, bacteria, fungus or other stress causing pathogens. These conditions pose a constant threat to the DNA integrity of these microorganisms and cause damage to their DNA, such as modified bases, mispaired bases, intrastrand crossbinding, interstrand crossbinding, pyrimidine dimers, single stranded breaks and double stranded breaks (DSBs). This consequently leads to cell death, thereby preventing the survival of these microorganisms in harsh environments. In order to overcome stress, these microorganisms are required to physiologically adapt themselves to such harsh environmental conditions. This may lead to loss of the unique traits of interest in these organisms. The low survival capacity and loss of unique traits of interest in these organisms are the major difficulties in exploiting their capabilities for industrial purposes.

The repair of DNA double strand breaks (DSBs) is essential to maintain the integrity of the genome. Un-repaired or improperly repaired DNA damage may result in genomic instability and eventually in cell death.

Many proteins are necessary for such DNA DSB—repair. One such important protein is Rad52 protein, which is necessary for accurate repair of DSBs and is highly conserved among eukaryotes, including animals, fungi and yeast. It also plays an auxiliary role with the replication protein A (RPA) in the action of Rad51 protein. Furthermore, Rad52 protein has an annealing activity and promotes the formation of D-loops in super helical DNA.

Disruption of RAD52 gene may cause severe recombination phenotype including extreme X-ray sensitivity, increased chromosome loss and failure to produce viable spores. Research on Rad52 mutants in *Saccharomyces cerevisiae* has revealed a critical role of Rad52 protein in double-strand break repair and meiosis. It has been revealed that in *Saccharomyces cerevisiae*, homologous recombination provides a major mechanism for eliminating DNA double-stranded breaks which may be induced by ionizing radiations or may be associated with injured DNA replication forks; and Rad52 protein plays a fundamental role in homologous recombination pathway and DNA double strand break repair.

WO2003089573 suggests a method of identifying compounds that induce a DNA repair pathway and/or inhibit retroviral cDNA integration into a host genome.

US20040111764 suggests an expression cassette comprising a meiotically active promoter operably linked to a polynucleotide encoding a recombinational DNA repair polypeptide or its fragment, which is capable of stimulating plant meiotic recombination when expressed into RNA and/or said polypeptide.

However, these conventional methods are typically incapable of enhancing the survival capacity of microorganisms along with enhanced biomass synthesis and simultaneously maintaining their genomic integrity in an effective and efficient manner, wherein confirmed stable transgene integration is being achieved. Additionally, some conventional methods employ a large number and/or quantity of chemicals in order to facilitate enhanced biomass synthesis.

Therefore, there exists a need to develop an efficient and effective method for enhancing the biomass synthesis capacity of a microorganism.

Objects

Some of the objects of the present disclosure, which at least one embodiment herein satisfies, are as follows:

It is an object of the present disclosure to provide a modified microorganism having enhanced biomass synthesis capacity.

It is another object of the present disclosure to provide a method for manufacturing a modified microorganism having an enhanced biomass synthesis capacity.

It is yet another object of the present disclosure to provide a method for manufacturing a modified microorganism having an enhanced DNA repair capacity in response to stress for achieving increased biomass.

It is still another object of the present disclosure to provide a method for over-expressing yeast RAD52 gene in a microorganism which is effective in inducing DNA repair in the microorganism.

It is yet another object of the present disclosure to provide an expression vector comprising a yeast RAD52 gene and a promoter capable of promoting the expression of said gene in DNA damaging conditions.

Other objects and advantages of the present disclosure will be more apparent from the following description, which is not intended to limit the scope of the present disclosure.

SUMMARY

In an aspect of the present disclosure there is provided a modified strain of *Chlamydomonas reinhardtii* CC125-45-03 having enhanced biomass synthesis capacity.

In another aspect of the present disclosure there is provided a method for enhancing biomass synthesis capacity in a microorganism, the method comprises the following steps: synthesizing a gene encoding a protein capable of inducing DNA repair; cloning said obtained gene along with a promoter capable of regulating the expression of said gene in DNA damaging conditions in an expression vector; introducing said expression vector comprising said gene and said promoter into a microorganism; growing said microorganism on a medium containing a selective agent; and exposing said microorganism to stress to facilitate overexpression of said gene and obtaining a microorganism with enhanced biomass synthesis capacity.

BRIEF DESCRIPTION OF THE ACCOMPANYING DRAWINGS

The method of the present disclosure will now be described with the help of the accompanying drawing, in which.

DETAILED DESCRIPTION

The conventional methods for inducing DNA repair in microorganisms are not effective in enhancing the biomass synthesis along with the DNA repair capacity in these organisms. Specifically, the conventional methods fail to address prolonged enhancement of the survival capacity of organisms in harsh environmental conditions including abiotic and biotic stresses, which pose a major threat to their DNA integrity and cause DNA damage leading to cell death. In order to overcome stress caused by such conditions, cells of the organisms are required to physiologically adapt themselves to the harsh environmental conditions, which may lead to a loss of the unique traits of interest in these organisms. Alternately, the cells may not be able to tolerate the stress at all.

The present disclosure therefore, provides a method for manufacturing a modified microorganism having an enhanced biomass synthesis capacity. The enhanced biomass synthesis capacity is a result of the overexpression of a gene capable of inducing DNA repair.

In the modified microorganism of the present disclosure, the DNA repair process initiates with the nucleolytic processing of the ends of DNA breaks to yield 3'ssDNA tails, which are bound by recombination factors to form nucleoprotein complex. This nucleoprotein complex then conducts a search to locate an undamaged DNA homologue and further catalyzes the formation of a DNA joint called the D-loop, with the homologue. The proteins encoded by evolutionarily conserved genes of the RAD52 group catalyze the homologous recombination reaction.

Figure 1:
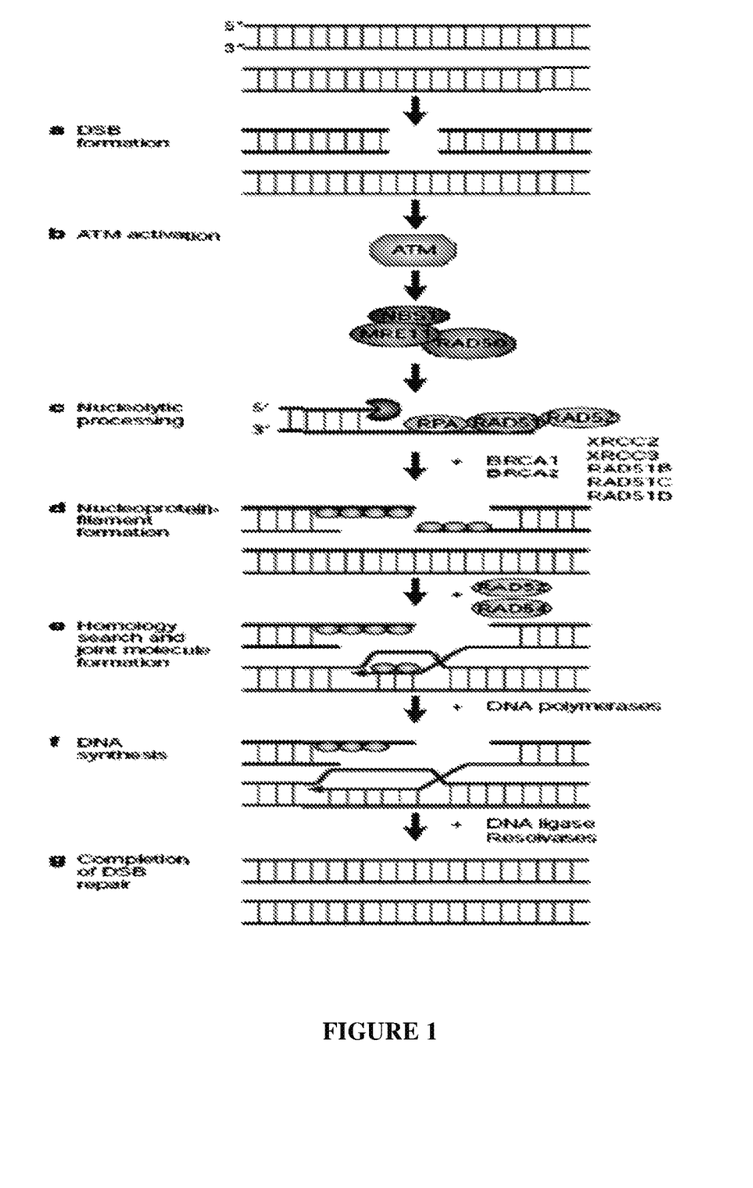
FIG. 1 illustrates a flow chart depicting the function of RAD52 in the method of the present disclosure.

Accordingly, in the present disclosure, a gene encoding a protein capable of inducing DNA repair is obtained. The function of RAD52 of the present method is illustrated as a flow chart in FIG. 1. In an embodiment of the present disclosure, the gene is yeast RAD52 gene encoding Rad52 protein. An example of the yeast in accordance with the present disclosure is *Saccharomyces cerevisiae*.

In accordance with one embodiment of the present disclosure, the gene is native yeast RAD52 gene. The expression of native yeast RAD52 gene is regulated by a suitable promoter. In accordance with one embodiment of the present disclosure, the promoter is a constitutive promoter. Alternatively, an inducible promoter is used in the present disclosure. The inducible promoter is capable of promoting the expression of the RAD52 gene at DNA damaging conditions.

In accordance with an embodiment of the present disclosure, the promoter is a non-yeast light inducible promoter (LIP). The promoter is at least one light inducible promoter selected from the group comprising *Dunaliella*, *Synechococcus elongatus* PCC 7942 and rbcS promoter.

In accordance with another embodiment of the present disclosure, the gene is recombinant yeast RAD52 gene.

Figure 2:
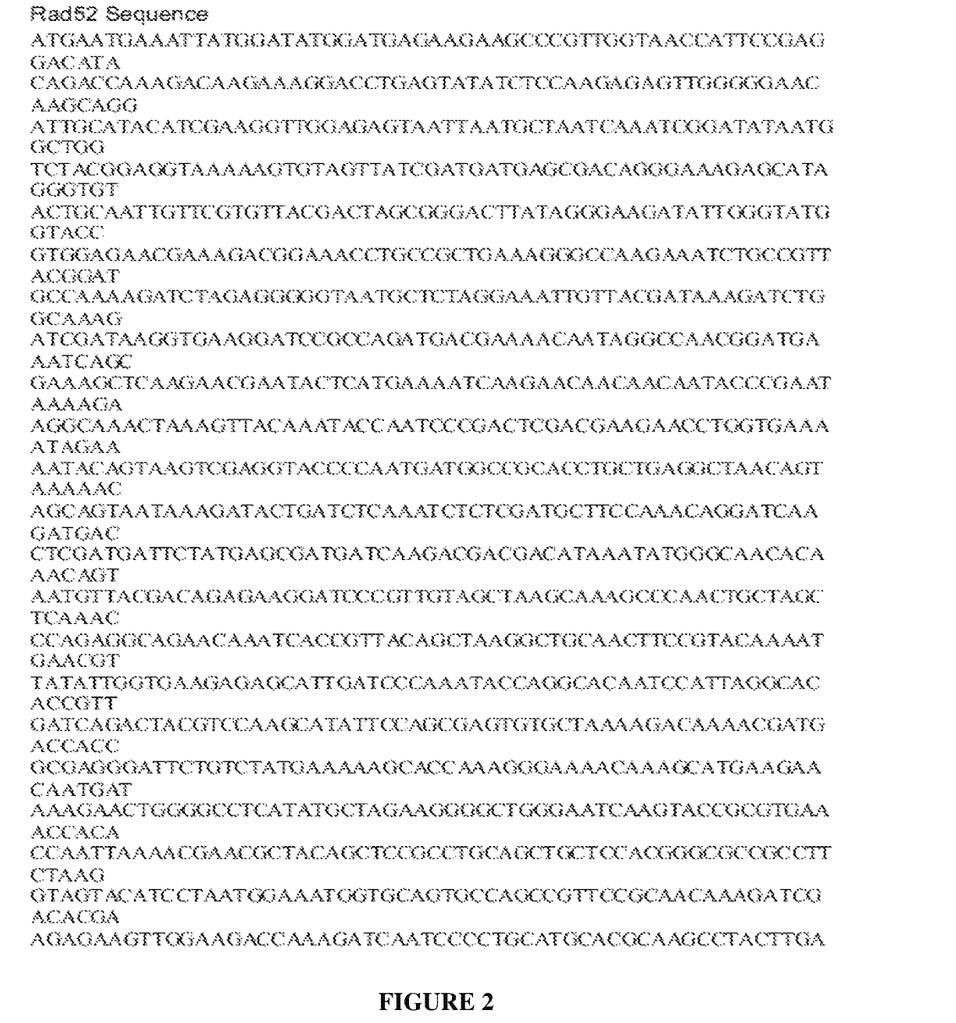
FIG. 2 illustrates the codon optimized sequence of RAD52.

The DNA sequence of the synthesized RAD52 (recombinant) gene comprises codons which are optimized for over-expression of said gene in a non-homologous host. The sequence of the codon optimized RAD52 gene with Sequence ID No. 1 is depicted in FIG. 2. The synthesized gene is then cloned in an expression vector. The expression vector includes but is not limited to a circular plasmid. Rad52 gene from *Saccharomyces cerevisiae* is cloned in the Not1 site of pChlamy_1. The pChlamy_1 vector containing the Rad52 gene from *Saccharomyces cerevisiae* is illustrated in FIG. 3 and FIG. 4.

Figure 3:
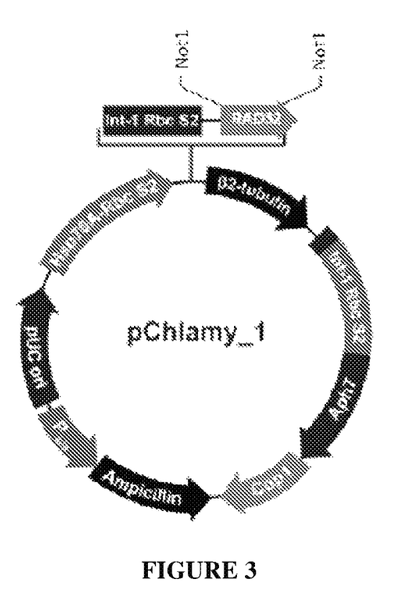
FIG. 3 illustrates the pChlamy_1 vector containing the RAD52 gene cloned in the Not1 site, and also containing the Hsp70A-RbcS2 Promoter.
Figure 4:
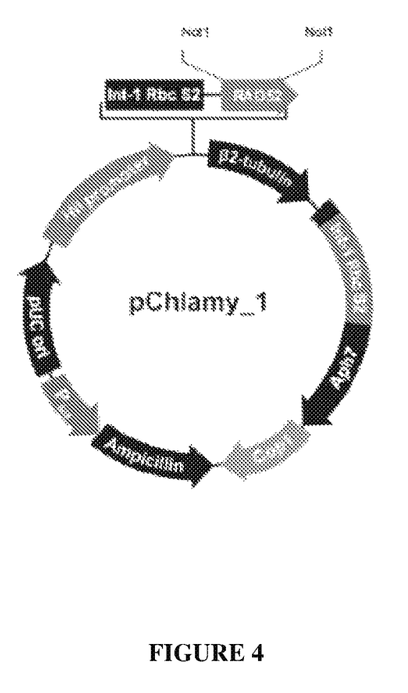
FIG. 4 illustrates the pChlamy_1 vector containing the RAD52 gene cloned in the Not1 site and also containing the High Light Inducible (Hli) promoter.

In accordance with one embodiment of the present disclosure, there is provided an expression vector comprising yeast RAD52 gene driven by either an Hsp70A-RbcS2 promoter (as illustrated in FIG. 3) or a high light inducible (Hli) promoter (as illustrated in FIG. 4).

The RAD52 gene-containing vector also contains a selectable marker. The selectable marker comprises a resistance agent possessing resistance to at least one compound selected from the group which includes but is not limited to an antibiotic compound, an antifungal compound and a toxic compound.

The cells of the untransformed microorganism are then transformed with the expression vector comprising the RAD52 gene to obtain modified microorganism. The cells of the untransformed microorganism are transformed with an expression vector by at least one method selected from the group which includes but is not limited to biolistics, *agrobacterium* mediated genetic transformation, and electroporation, preferably electroporation.

In accordance with the present disclosure, the microorganism may be a prokaryotic microorganism which includes but is not limited to bacteria. The organism may be a eukaryotic organism which includes but is not limited to plants. The organism may be a photosynthetic organism which includes but is not limited to plants and algae.

In a preferred embodiment of the present disclosure, the microorganism is an alga. Alga when used according to the present disclosure is selected from the group including but not limited to *Dunaliella*, *Chlorella*, *Nannochloropsis* and *Chlamydomonas*.

The modified microorganism is cultured on a medium containing at least one selective agent. The selective agent is at least one compound selected from the group comprising an antibiotic compound, an antifungal compound and a toxic compound. The selection agent is at least one antibiotic compound selected from the group which includes but is not limited to zeocin, kanamycin, chloramphenicol, and hygromycin, preferably hygromycin. In a preferred embodiment of the present disclosure, the amount of hygromycin in the medium is 60 mg/liter.

Preferably, the culture of the modified microorganism is incubated after transformation for a time period of 10 to 48 hours before being plated on the medium containing a selective marker.

The modified microorganisms are selected and isolated based upon the expression of the selectable marker. The modified microorganisms are screened by molecular analysis and those resistant to the selective agent are isolated.

In accordance with another embodiment of the present disclosure, the method for manufacturing a modified microorganism having an enhanced biomass synthesis capacity in response to stress, further comprises the steps which are described herein below:

The isolated modified microorganisms are cultured in a selection medium comprising hygromycin after 12 to 24 hours of isolation, for a time period of 15 to 20 days.

The progeny of the modified microorganism is then isolated to obtain a modified microorganism having a gene to induce DNA repair in the microorganism in DNA damaging conditions. The progeny of modified microorganism is analyzed for stable integration of yeast RAD52 gene by at least one method which includes but is not limited to Polymerase Chain Reaction, Southern Blot and Northern Blot. This is followed by isolation of the modified microorganism containing RAD52 gene.

The modified microorganism obtained by the method of the present disclosure contains RAD52 gene, which is over-expressed to induce DNA repair in the microorganism in DNA damaging conditions to provide a modified microorganism having an enhanced biomass synthesis capacity as a result of overexpression of the gene capable of inducing DNA repair mechanism. The RAD52 gene is expressed when DNA damage is most and the DNA repair machinery is required.

In accordance with another aspect of the present disclosure, there are provided modified strains of prokaryotes and or eukaryotes, specifically modified strains of algae and/or cyanobacteria with increased biomass synthesis capacity, particularly, a modified strain in accordance with the present invention can be *Chlamydomonas reinhardtii* CC125-45-03 deposited in the Culture Collection of Algae and Protozoa (CCAP), SAMS Limited, Scottish Marine Institute, Dunbeg Oban, Argyll, PA37 1QA, UK, on 13 Jan. 2015, accepted for deposit for patent purposes on 26 Jan. 2015 and having CCAP Accession Number 11/172.

The modified microorganism manufactured in accordance with the present disclosure has a specific promoter which regulates the expression of RAD52; whereby RAD52 is overexpressed resulting in increased biomass synthesis as a result of the enhanced DNA repair in the modified microorganism. A 5-fold increase in viability can be achieved in the modified microorganism. The transformants (RAD52 gene is over-expressed to induce DNA repair) of the present disclosure and wild type are treated with UV light and then allowed to grow. An initial decrease in the growth is observed due to the damage to DNA, but the transformants recover much faster as compared to the wild type as illustrated by the OD measured at 750 nm. The enhanced DNA repair capacity is due to the over-expression of the RAD52 gene.

The present disclosure will now be described in the light of the following non-limiting examples:

Example 1: Transformation of *Chlamydomonas* Using Electroporation Method

*Chlamydomonas* cells (Invitrogen) were grown in Tris Acetate Phosphate (TAP) media (Invitrogen) at a temperature of 20° C. for 4 to 6 days. After the completion of growth, 10% Tween 20 was added to $4 \times 10^8$ cells of *Chlamydomonas*. The cells were centrifuged at 200 rpm at a temperature of 4° C. for 5 minutes. The cells were then re-suspended in ice-cold 4 ml TAP medium containing 40 mM sucrose solution. 2.5 micrograms of pChlamy_1 plasmid (Invitrogen) containing the Rad52 gene along with High Light Inducible (Hli) promoter was linearised by restriction digestion and the plasmid DNA was dissolved in 30 µl TAP medium containing 40 mM sucrose solution. 50 µg of salmon sperm DNA dissolved in 5 µl of water (10 µg/µl) was used as a carrier and denatured by heating at a temperature of 95° C. The salmon sperm DNA solution (in water) was then added to the cell suspension followed by the addition of the plasmid DNA prepared as described above to the cell suspension. A final volume of 250 microliters of the above mixture comprising cell suspension, plasmid DNA & carrier salmon sperm DNA was taken in a 4 mm cuvette and electroporation was performed using 720-920 volts, 10 microfarads capacitance using Biorad electroporator. After electroporation, cells were kept in a water bath at 25° C. for 12 hours. The cells were then plated on TAP media containing 40 mM sucrose solution. 0.5% agarose, 1 ml 20% corn starch, 0.4% polyethylene glycol and 10 µg/ml hygromycin was added to the TAP medium containing 40 mM sucrose solution. Transformants were obtained and re-streaked on hygromycin containing medium for further confirmation.

Example 2: Comparison of Transformed *Chlamydomonas* and Control Response to Stress $10^7$ cells of transformed *Chlamydomonas* obtained by the method of Example 1 and control without Hli-Rad52 were grown in 3 ml of Tris Acetate Phosphate (TAP) media (Invitrogen) for 3 days. After the completion of the growth, both the transformed *Chlamydomonas* and the control were exposed to 100,000 lux for 3 hours. After 3 hours, the cells were allowed to grow at normal conditions having a light intensity of 10,000 lux.

After 3 to 4 days, the control culture showed a color change from green to white due to bleaching/cell death. The control culture could not adapt to the stress and could not survive after 3 to 4 days. In contrast, the culture of the transformed *Chlamydomonas* retained the green color indicating that it was able to adapt to the stress and survive. The transformed *Chlamydomonas* cells were able to survive for 15 to 20 days, indicating approximately a 5-fold increase in viability in the transformed *Chlamydomonas*.

Example 3: Comparison of Wild Type (WT) and Transformed *Chlamydomonas* to UV Light Treatment Five *Chlamydomonas* transformants obtained by the method of Example 1 and WT cultures without Rad52 were taken for this study. The five transformants and WT culture were inoculated in 20 ml TAP media (Invitrogen) and incubated under continuous light till a cell density of $10^6$ cell/ml was obtained (approximately 0.1 OD at 750 nm). After the completion of growth the transformants and the WT culture were transferred to multi-well plates having 6 wells. The transformants and the WT culture were illuminated by 2500 pJoules·$m^{-2}$·$s^{-1}$ of UV. After the cultures were exposed to UV light, both the transformants and the WT culture were incubated in the dark for 24 hours. Next, the transformants and the WT culture were incubated at 25° C., a light intensity of 100 µE·$m^{-2}$·$s^{-1}$ and a light:dark cycle of 12:12 hours.

Figure 5:
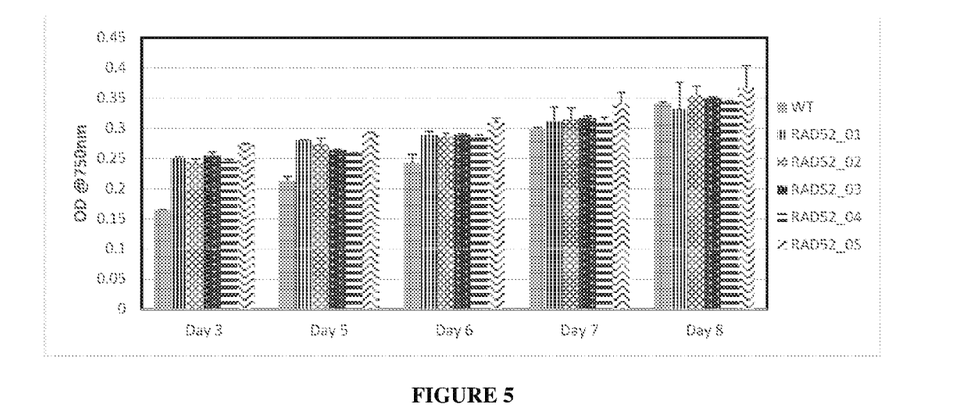
FIG. 5 illustrates the growth of wild type and transformants without UV treatment.

Similar plate of transformants and WT culture was incubated without the UV treatment. The experiment was conducted in duplicate and the average was taken for plotting graph. FIG. 5 illustrates the growth of wild type and transformants without UV treatment incubated at 25° C., a light intensity of 100 $\rho E \cdot m^{-2} \cdot s^{-1}$ and a light:dark cycle of 12:12 hours. As depicted in FIG. 5, both the WT and the transformants show similar growth rates over a period of 8 days.

Figure 6:
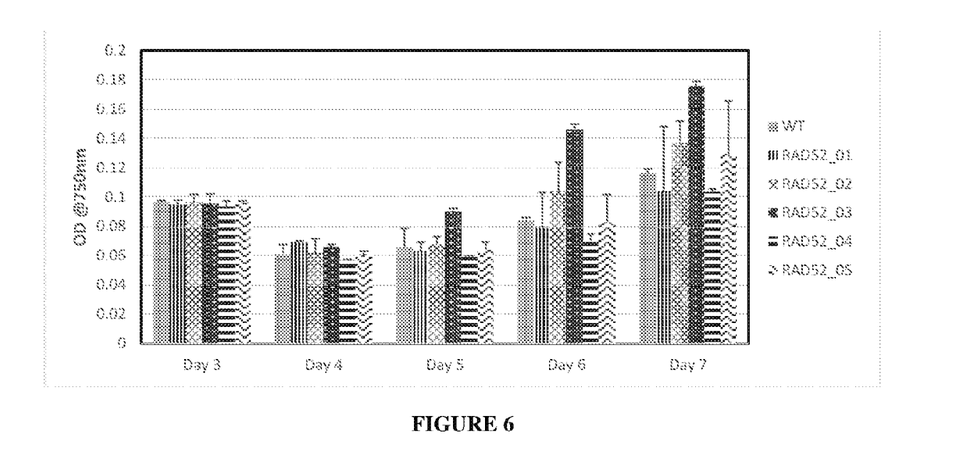
FIG. 6 illustrates the growth of wild type and transformants after UV treatment.

FIG. 6 illustrates the growth of wild type and transformants given UV treatment (2500 $\rho Joules \cdot m^{-2} \cdot s^{-1}$) and then incubated at 25° C., a light intensity of 100 $\rho E \cdot m^{-2} \cdot s^{-1}$ and a light:dark cycle of 12:12 hours. As depicted in FIG. 6, initially (Day 4) a decrease in the OD of both WT and transformants was observed. After 4 days the cultures start recovering and growing resulting in an increase in the OD. The numerical values of the OD values of the WT and three of the transformants is given in Table 1 below. It is clearly seen from FIG. 6 and Table 1, that three of the transformants RAD_02. RAD_03 and RAD_05 show an increase in the OD as compared to the wild type, thereby indicating increased biomass of the transformants as compared to the wild type. The recovery is faster in transformants as compared to the wild type as depicted in FIG. 6.

TABLE 1

Numerical OD values as seen in FIG. 6 of the drawings

| | OD@750 nm on Day 7 | % Increase in OD value as compared to WT |
|---|---|---|
| WT | 0.116 | NA |
| RAD52_02 | 0.137 | 18% |
| RAD52_03 | 0.176 | 51% |
| RAD52_05 | 0.129 | 11% |

It would be appreciated by a person of ordinary skill in the art that suitable modifications may be carried out in the method of the present disclosure and still achieve the results as those achieved by the method of the present disclosure. Such modifications by virtue of their nature are a part of the present disclosure. The method provided herein is illustrative and does not rule out such modifications.

Economic Significance and Technical Advancement

The technical advancements offered by the present disclosure are as follows:

The present disclosure provides a modified microorganism having enhanced biomass synthesis capacity.

The present disclosure provides a method for manufacturing a modified microorganism having enhanced biomass synthesis capacity.

The method of the present disclosure is simple, efficient and cost-effective due to use of lesser number of chemicals (as opposed to some conventional methodologies) and use of efficient strain(s) constructed having enhanced biomass synthesis capacity.

While considerable emphasis has been placed herein on the preferred embodiments, it will be appreciated that many embodiments can be made and that many changes can be made in the preferred embodiments without departing from the principles of the disclosure. These and other changes in the preferred embodiments as well as other embodiments of the disclosure will be apparent to those skilled in the art from the disclosure herein, whereby it is to be distinctly understood that the forgoing descriptive matter is to be implemented merely as illustrative of the disclosure and not as limitation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

Any discussion of documents, acts, materials or the like that has been included in this specification is solely for the purpose of providing a context for the invention. It is not to be taken as an admission that any or all of these matters form part of the prior art base or were common general knowledge in the field relevant to the invention as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

The invention claimed is:

1. A method for enhancing biomass synthesis capacity in a microorganism, said method characterized by the following steps:
   a. synthesizing a gene encoding a protein capable of inducing DNA repair;
   wherein said gene is a yeast RAD52 gene encoding Rad52 protein, selected from the group consisting of native yeast RAD52 gene and recombinant yeast RAD52 gene;
   b. cloning said synthesized gene along with a promoter capable of regulating the expression of said gene in DNA damaging conditions in an expression vector;
   c. introducing said expression vector comprising said gene and said promoter into the microorganism;
   d. growing said microorganism in a medium containing a selective agent; and
   e. exposing said microorganism to stress to facilitate overexpression of said gene and obtaining the microorganism with enhanced biomass synthesis capacity.

2. The method of claim 1, wherein said yeast is *Saccharomyces cerevisiae* and wherein the yeast RAD52 gene is a codon optimized gene with Sequence ID No. 1.

3. The method of claim 1, wherein said microorganism in step (c) is selected from the group comprising prokaryotes and eukaryotes, preferably a photosynthetic microorganism.

4. The method of claim 1, wherein said microorganism is an alga, selected from the group comprising *Dunaliella, Chlorella, Nannochloropsis* and *Chlamydomonas*.

5. The method of claim 1, wherein said promoter is at least one light inducible promoter selected from the group comprising *Dunaliella, Synechococcus elongatus* PCC 7942 and rbcS promoter.

6. The method of claim 1, wherein said expression vector is pChlamy_1.

7. The method of claim 1, wherein said selective agent in the medium is at least one compound selected from the group comprising antibiotic compound, antifungal compound and toxic compound.

8. The method of claim 1, wherein said antibiotic compound is at least one selected from the group consisting of zeocin, kanamycin, chloramphenicol and hygromycin.

9. The method of claim 1, wherein in step (e), said microorganism is exposed to at least one stress selected from the group comprising ultraviolet radiation (UV), salinity, light, unfavorable temperature, alkalinity, nutrient limitation, oxidative stress, senescence, sulfur deficiency, carbon deficiency, nitrogen use inefficiency, virus, bacteria and fungus.

10. A method for manufacturing a modified microorganism having enhanced biomass synthesis capacity, said method comprising by the following steps:
   a. synthesizing a gene encoding a protein capable of inducing DNA repair;
   wherein said gene is a yeast RAD52 gene encoding Rad52 protein, selected from the group consisting of native yeast RAD52 gene and recombinant yeast RAD52 gene;
   b. cloning said synthesized gene along with a promoter capable of regulating the expression of said gene in DNA damaging conditions in an expression vector;
   c. introducing said expression vector comprising said gene and said promoter into the microorganism;
   d. growing said microorganism on a medium containing a selective agent; and
   e. exposing said microorganism to stress to facilitate overexpression of said gene to obtain the microorganism having enhanced biomass synthesis capacity,
   wherein, the biomass synthesized by the modified microorganism is increased relative to the unmodified microorganism.

11. A method for increasing algal biomass; said method comprising the following steps:
   a. synthesizing a gene encoding a protein capable of inducing DNA repair;
   wherein said gene is a yeast RAD52 gene encoding Rad52 protein, selected from the group consisting of native yeast RAD52 gene and recombinant yeast RAD52 gene;

b. cloning said synthesized gene along with a promoter capable of regulating the expression of said gene in DNA damaging conditions in an expression vector;
c. introducing said expression vector comprising said gene and said promoter into an alga
d. growing said alga in a medium containing a selective agent; and
e. exposing said alga to stress to facilitate overexpression of said gene to obtain enhanced algal biomass.

12. A modified microorganism manufactured by the process claimed in claim 10.

13. A modified strain of *Chlamydomonas reinhardtii* CC125-45-03 having CCAP Accession Number 11/172.

14. The method of claim 8, wherein the antibiotic compound comprises hygromycin.

* * * * *